(12) United States Patent
Van Doorn et al.

(10) Patent No.: US 11,590,040 B2
(45) Date of Patent: Feb. 28, 2023

(54) SLIDING ACCESSORY RAIL FOR HOLDING EQUIPMENT AT A PATIENT SUPPORT

(71) Applicant: KONINKLIJKE PHILIPS N.V., Eindhoven (NL)

(72) Inventors: Andre Van Doorn, Best (NL); Walter Peter Bleyen, Lommel (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/483,819

(22) PCT Filed: Feb. 2, 2018

(86) PCT No.: PCT/EP2018/052720
§ 371 (c)(1),
(2) Date: Aug. 6, 2019

(87) PCT Pub. No.: WO2018/146026
PCT Pub. Date: Aug. 16, 2018

(65) Prior Publication Data
US 2020/0022860 A1    Jan. 23, 2020

(30) Foreign Application Priority Data
Feb. 7, 2017 (EP) .................. 17154913

(51) Int. Cl.
*A61G 13/10* (2006.01)
*A61B 90/57* (2016.01)

(52) U.S. Cl.
CPC ............ *A61G 13/101* (2013.01); *A61B 90/57* (2016.02); *A61B 2090/571* (2016.02)

(58) Field of Classification Search
CPC ...... A61G 13/101; A61B 90/57; A61B 90/571
See application file for complete search history.

(56) References Cited

U.S. PATENT DOCUMENTS

| | | | | |
|---|---|---|---|---|
| 3,046,072 A | * | 7/1962 | Douglass, Jr. | ......... A61G 13/12 600/230 |
| 4,901,964 A | | 2/1990 | McConnell | |
| 5,077,780 A | * | 12/1991 | Lee, Jr. | ................ A61B 6/0442 378/196 |

(Continued)

FOREIGN PATENT DOCUMENTS

| | | |
|---|---|---|
| DE | 202009007202 U1 | 9/2009 |
| DE | 102013105374 A1 | 11/2014 |

(Continued)

OTHER PUBLICATIONS

PCT/EP2018/052720 ISR & Written Opinion, dated Apr. 25, 2018, 14 Pages.

*Primary Examiner* — David R Hare

(57) ABSTRACT

The present invention relates to holding equipment at an operating table. In order to removably provide equipment at a patient support, a holding device (10) is provided that comprises an accessory rail (12) and at least a first portion (14) of a coupling is provided. The accessory rail is configured as an attachment interface (16) for temporal attachment of equipment (18) at a patient support (20). The accessory rail is rigidly connected to the first portion of the coupling. The first portion of the coupling is configured to provide, in interaction with a second portion (22) of the coupling, a movable connection for connecting the accessory rail to a patient support, wherein the movable connection is configured to provide a horizontal sliding movement of the accessory rail in relation to the patient support. The provision of a movable connection allows, for example, to temporarily move or even remove the accessory rail together with mounted equipment. For example, during an intervention procedure, for certain phases, the equipment is not needed or a different configuration is needed, and wider access to the patient is required. The equipment can then easily be removed and put back in place.

17 Claims, 3 Drawing Sheets

(56) References Cited

U.S. PATENT DOCUMENTS

| | | | | |
|---|---|---|---|---|
| 5,135,210 | A * | 8/1992 | Michelson | A61G 13/12 5/658 |
| 5,287,575 | A * | 2/1994 | Allen | A61G 13/101 248/231.41 |
| 6,022,143 | A * | 2/2000 | Helmreich | A61B 6/00 378/181 |
| 6,023,800 | A * | 2/2000 | Stickley | A61G 7/0507 248/229.26 |
| 6,499,158 | B1 * | 12/2002 | Easterling | A61G 15/10 248/231.61 |
| 6,564,406 | B2 * | 5/2003 | VanSteenburg | A61G 13/12 5/621 |
| 6,598,275 | B1 * | 7/2003 | Kolody | A61G 13/101 24/455 |
| 6,678,908 | B2 | 1/2004 | Borders | |
| 7,210,180 | B2 * | 5/2007 | Malcolm | A61G 13/125 5/663 |
| 8,621,692 | B1 * | 1/2014 | Kring | A61G 13/101 5/503.1 |
| 8,782,832 | B2 * | 7/2014 | Blyakher | A61B 6/0421 5/601 |
| 2004/0223806 | A1 * | 11/2004 | Seufert | A61B 6/04 403/317 |
| 2005/0004470 | A1 * | 1/2005 | Camus | A61G 13/101 600/459 |
| 2009/0169831 | A1 | 7/2009 | Malcolm | |
| 2011/0064548 | A1 * | 3/2011 | Wrolson | F16M 13/022 414/349 |
| 2014/0007408 | A1 * | 1/2014 | Nool | A61M 5/1418 29/525.01 |
| 2014/0059773 | A1 * | 3/2014 | Carn | A61G 13/123 5/624 |
| 2014/0205371 | A1 * | 7/2014 | Bally | A61G 12/005 403/327 |
| 2014/0215718 | A1 | 8/2014 | Wootton | |
| 2014/0238408 | A1 * | 8/2014 | Shepherd | A61G 13/1235 128/845 |
| 2016/0076566 | A1 | 3/2016 | Vogtherr | |
| 2016/0287461 | A1 * | 10/2016 | Naughton | A61G 13/08 |
| 2018/0028387 | A1 * | 2/2018 | Yellin | A61B 90/50 |
| 2018/0085270 | A1 * | 3/2018 | Elias | A61G 13/1245 |
| 2019/0083183 | A1 * | 3/2019 | Moll | A61B 50/10 |
| 2019/0262206 | A1 * | 8/2019 | Yancey | A61G 13/101 |

FOREIGN PATENT DOCUMENTS

| | | |
|---|---|---|
| WO | 0065955 A2 | 11/2000 |
| WO | 2016071092 A1 | 5/2016 |

* cited by examiner

SLIDING ACCESSORY RAIL FOR HOLDING EQUIPMENT AT A PATIENT SUPPORT

CROSS-REFERENCE TO PRIOR APPLICATIONS

This application is the U.S. National Phase application under 35 U.S.C. § 371 of International Application No. PCT/EP2018/052720, filed on Feb. 2, 2018, which claims the benefit of European Patent Application No. 17154913.2, filed on Feb. 7, 2017. These applications are hereby incorporated by reference herein.

FIELD OF THE INVENTION

The present invention relates to a holding device, to a system for holding equipment at a patient support and to a method for removably providing equipment at a patient support.

BACKGROUND OF THE INVENTION

In a hospital, healthcare or medical environment different types of devices and equipment may need to be provided at a patient table. Equipment is mounted, for example, to a rail lateral to the patient table. For example, U.S. Pat. No. 6,023,800 describes a detachable siderail that may be clamped onto the side edge of a surgical table top. For example, US 2005/0004470 A1 describes an ultrasound head mounting that engages, with a bracket, a mounting-side adapter rail that is connected to a table-side adapter piece via a mounting element for level compensation. The adapter piece has a hook attachment for an accessory rail of the patient positioning table. For example, DE 20 2009 007202 U1 describes a holding device for mounting of equipment to a holding rail of an operation table. In an example, an additional rail is attached to a first rail by two holding brackets, as the first rail is covered by a sterile cloth. For example, DE 10 2013 105374 A1 describes an adapter device for an operation table. The adapter device comprises a rail segment for detachably mounting of equipment. The adapter device is attachable to a siderail of an operation table and allows for a rotatable adjustment of the rail segment. To fulfill certain requirements during medical interventions, it may occur that devices need to be relocated in the range of a physician, or different types of equipment or modules may be needed. US 2004/0223806 describes a fastening system for fastening an object or an accessory on a patient table. Nevertheless, the mounting and demounting steps may lead to damage of the modules when they are needed at different location at the table and the relocating may impair the physician during work.

SUMMARY OF THE INVENTION

There may thus be a need to further improve the relocation process of equipment.

The object of the present invention is solved by the subject-matter of the independent claims; further embodiments are incorporated in the dependent claims. It should be noted that the following described aspects of the invention apply also for the holding device, for the system for holding equipment at a patient support and for the method for removably providing equipment at a patient support.

According to the present invention, a holding device is provided. The holding device comprises an accessory rail and at least a first portion of a coupling. The accessory rail is configured as an attachment interface for temporal attachment of equipment at a patient support, for example during an intervention or another examination procedure. The accessory rail is rigidly connected to the first portion of the coupling. The first portion of the coupling is configured to provide, in interaction with a second portion of the coupling, a movable connection for connecting the accessory rail to a patient support. The movable connection is configured to provide a horizontal sliding movement of the accessory rail in relation to the patient support.

As an effect, the sliding movement provides e.g. the option of moving a whole set of modules. The equipment modules and the attached cables of the equipment modules are thus less exposed to wear during the relocation process which would result in lower uptime. Further, potential cable clutter is avoided and the (temporarily) shifting of the equipment and devices is less time consuming. Also, the sliding movement enables the temporary removal of equipment and devices from an area around the patient, for example to enable adjustments of equipment and devices by support personnel without interfering with medical personnel attending to the patient on the table.

The term "horizontal" sliding movement refers to a sliding movement in a direction aligned with the surface of the patient table on which a patient may be resting. The term "horizontal" thus refers to a direction with no inclination with respect to the patient table surface, for example an absolutely horizontal direction in line with the plane. Alternatively, a "horizontal" movement may be a movement in a direction with a deviation of e.g. up to +/−20° in relation to the plane, for example up to +/−15°, up to +/−10° or up to +/−5°. The equipment can be mounted on the accessory rail. The accessory rail is connected to the first portion, which provides the coupling with the second portion. The second portion then provides the mounting to the patient support.

According to an example, the movable connection is configured to provide the horizontal sliding movement of the accessory rail with attached equipment.

According to an example, the holding device further comprises a second portion of the coupling forming the coupling together with the first portion of the coupling. The first portion of the coupling is movable in relation with the second portion, and the second portion of the coupling is configured to be attached to the patient support.

As a result, the necessary mounting steps for the installation and/or relocation of equipment may be reduced. Furthermore, this results in less damage due to the movement of the modules.

According to an example, the first portion of the coupling is configured to provide, in interaction with the second portion of the coupling, a fixation for temporary fixing of the accessory rail in relation to the patient support.

In an example, the movable connection also provides the fixation for temporary fixing of the accessory rail in relation to the patient support.

This allows a precise arrangement of equipment.

In an example, the coupling is configured to be stationary attached to the patient support.

According to an example, the second portion of the coupling is a mounting rail configured to be attached to the patient support. The accessory rail is shiftable at least partly outside a range of the mounting rail to enlarge a range of mounted equipment.

In an example, the second portion of the coupling is a mounting rail attached to a patient support; and the accessory rail is shiftable at least partly outside a range of the mounting rail attached to the patient support to elongate the range of the equipment.

In an example, the accessory rail is shiftable at least partly outside a range of the second portion of the coupling the fixed accessory rail to elongate the range of the equipment.

The term "range" refers to the length of the rail to which the accessory rail is mounted. The so-to-speak two-rail solution allows an increased range for the arrangement of the equipment. For example, a parking position for equipment currently not used or required can be provided, which parking position can be outside the range of the rail mounted to the patient support. For use of the equipment, the accessory rail is moved in a sliding manner to re-arrange the equipment near the patient.

According to an example, the first and/or second portion of the coupling comprises a rail.

In an example, the accessory rail provides an attachment length of at least the half of the patient table's length, for example an attachment length corresponding to a majority of the patient table's length.

According to an example, the first portion of the coupling comprises an accommodation for a further rail with a profile as the accessory rail; and the second portion of the coupling comprises a further rail with a profile of the accessory rail.

In an example, the accessory rail is movably connected to the further rail that has a similar or same shape, i.e. contour, as the accessory rail. In other words, both rails have the same contour and coupling of the equipment to the accessory rail is the same as coupling of the accessory rail to the further rail.

According to an example, the accessory rail is configured with a first cross-section or profile in order to provide a first type of coupling interface for mounting of equipment; and the first portion of the coupling provides a second type of coupling interface to be mounted to a second cross-section or profile. Further, the holding device serves as an adapter between the first and the second type of coupling interface.

In an example, the first cross-section or profile is a standard profile, e.g. a European standard or a standard profile commonly used in the US. The second standard cross-section or profile can also be a standard profile, such as the standard used in the US or the European standard.

The second portion of the coupling can also be provided as a fixed accessory rail. If the fixed accessory rail is provided with a profile and dimensions according to one specific standard, and equipment according to a different standard should be mounted, the further accessory rail can be provided according to this different standard.

According to the invention, also a system for holding equipment at a patient support is provided. The system comprises a patient support. The system also comprises a holding device according to one of the examples above. Equipment is attachable to the accessory rail, and, in relation to the patient support, the accessory rail is movable in a horizontal sliding movement.

In an example, the equipment is provided as an equipment assembly with different equipment components arranged on the accessory rail. The equipment assembly can be moved in relation to the patient support by the horizontal sliding movement provided by the holding device.

In another example, the equipment is provided as an equipment arrangement. The equipment arrangement is removably attached to the holding device and the holding device removably attached to the patient support. The equipment arrangement comprises at least one of the group of: monitor units, X-ray imaging units, ultrasound units, patient monitoring units and interventional tool operating units.

The system for holding equipment at a patient support can also be referred to as "holding system".

In an example, the equipment arrangement could comprise one or more of these devices.

According to an example, the system further comprises equipment. The equipment is removably attached to the accessory rail of the holding device. The equipment comprises at least one of the group of: monitor units, X-ray imaging units, ultrasound units, patient monitoring units and interventional tool operating units.

According to an example, an arrangement of the equipment is provided on the accessory rail in a mounted configuration. The arrangement of the equipment is movably in a horizontal sliding movement and/or detachably from the patient support while maintaining the mounted configuration on the accessory rail.

The term "mounted configuration", also referred to as mounting configuration" or "mounted arrangement", relates to a certain (spatial) arrangement of different components of the equipment.

The equipment that is provided on the accessory rail can stay fixed, i.e. attached in the mounted configuration on the accessory rail, since the accessory rail is detachable together with the mounted equipment. Instead of having to de-mount all components individually, the components of the equipment remain their relative positions and can also keep their supply and data connections. This results in faster turn-around times when switching between different scenarios that occur during an intervention or examination procedure.

According to an example, at least one further accessory rail is provided that is connected to a further first portion of the coupling, and the further accessory rail is provided to be equipped with a further arrangement of the equipment provided on the accessory rail in a further mounted configuration.

As a result, different configurations can be prepared and due to being mounted on different accessory rails, the configurations can easily be replaced or exchanged.

In an example, at least one further holding device is provided.

As an effect, a full set of equipment may be substituted, wherein a perceptible saving of time can be achieved.

According to the invention, also a method for removably providing equipment at a patient support is provided. The method comprises the following steps:

a) providing an accessory rail that is rigidly connected to a first portion of a coupling of a holding device; wherein the accessory rail is configured as an attachment interface for temporal attachment of equipment at a patient support;
b) coupling the first portion to a second portion of the coupling attached to the patient support, such that, in interaction with the second portion of the coupling, a movable connection of the accessory rail to the patient support is provided; and
d) horizontally sliding of the accessory rail in relation to the patient support.

In an example, the equipment is attached and provided to a user during a medical intervention. The attachment process may take place before the intervention, but equipment can also be attached during an intervention. The accessory rail can be shifted and fixed during the intervention.

According to an example, it is further provided:
c1) temporal attaching of equipment at a patient support by the attachment interface of the accessory rail; and/or c2) fixating of the accessory rail for temporary fixing of the accessory rail in relation to the patient support.

According to an example, it is further provided:

e) substituting the accessory rail with a further accessory rail.

According to an aspect, a movable rail is attached to a patient support, like a patient table, to allow moving of mounted equipment. The movable rail can be fixed for providing secure mount of the equipment. In an option the movable rail is mounted onto an existing fixed rail.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
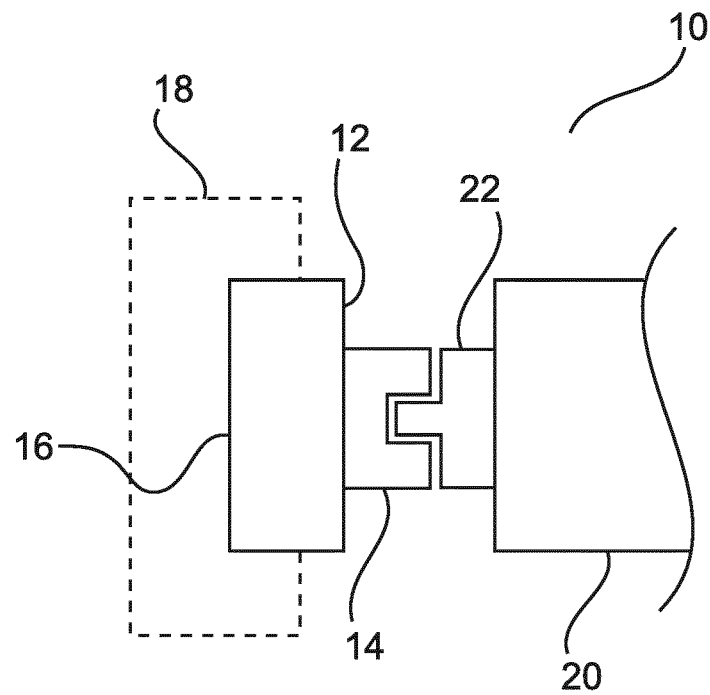
FIG. 1 shows a schematic vertical cross-section view of an example of a holding device.

FIG. 1 shows a holding device 10 comprising an accessory rail 12 and at least a first portion 14 of a coupling. The accessory rail 12 is configured as an attachment interface 16 for temporal attachment of equipment 18 at a patient support 20, e.g. during intervention.

The accessory rail 12 is rigidly connected to the first portion 14 of the coupling. The first portion 14 of the coupling is configured to provide, in interaction with a second portion 22 of the coupling, a movable connection for connecting the accessory rail 12 to a patient support, wherein the movable connection is configured to provide, as a shifting movement, a horizontal sliding movement of the accessory rail 12 in relation to the patient support 20.

In an example, the movable connection is configured to provide the horizontal sliding movement of the accessory rail with attached equipment.

As an option, the first portion 14 of the coupling is configured to provide, in interaction with the second portion 22 of the coupling, a fixation for temporary fixing of the accessory rail in relation to the patient support.

In an example, the holding device further comprises the second portion 22 of the coupling forming the coupling together with the first portion of the coupling. The first portion 14 of the coupling is movable in relation with the second portion 22, and the second portion 22 of the coupling is configured to be attached to the patient support.

In an example, not shown in detail, a fixation mechanism is provided. For example, the coupling has a brake or locking mechanism that is provided to interact, e.g. clamp or engage with a counterpart arranged on the patient support. For example, if the accessory rail is movably mounted to a further rail, the brake mechanism can have clamping portions that act on the further rail to achieve fixation. The mechanism can also have locking members that are engaging with recesses in the further rail to achieve a (temporarily) locked state.

Since the equipment 18, such as different modules for certain tasks, can maintain mounted on the accessory rail 12, it is also possible to maintain energy and data connections, for example in form of cables. To be able to keep the equipment 18 mounted to the accessory rail 12 thus facilitates the logistic setup. For example, the movable accessory rail 12 provides a possibility to keep the equipment 18 connected with their cables (for both data and energy supply) and thus avoids cable clutter that could otherwise occur when taking the equipment 18 off the rail, moving the equipment 18 and putting the equipment 18 back in place. Cables are thus exposed less to wear and damage, which results in a higher uptime and lifetime.

As a further aspect, the necessary mounting steps for the installation and/or relocation of equipment 18 may be reduced, which results in less damage due to the common moving or handling of the modules of equipment.

The provision of a movable connection of the accessory rail 12 further allows, for example, to quickly provide free moving space for the surgeon, for example, by sliding all equipment 18 or modules together to the side when, for example, the equipment 18 is not needed, or needed at a different place, or the space occupied by the modules is temporarily needed for another activity such as placing the patient on a patient support 20, such as an operating table. The initial distances between the modules, which distances may be provided in an optimal manner, will be kept the same, e.g. in order to reduce preparation time compared to a situation where all modules are individually moved or removed and repositioned.

The "equipment" can also be referred, in particular, as "medical equipment" and relates to modules such as, for example, displays, investigation devices, operating supply modules. The term "equipment" relates to devices and arrangements that are used during a medical intervention, for example to support the intervention, e.g. the surgeon or physician or the patient. For example, the "equipment" provides monitoring or supplying of the patient, or serves for displaying information or providing a user interaction possibility. The term "equipment" may also relate to control devices or interfaces used during an operation. The term "equipment" thus relates to all kind of support that is provided at the site of the intervention or operation and the support being mounted at the patient table.

The first portion 14 of the coupling can also be referred to as a "coupling". The second portion 22 of the coupling can also be referred to as a "mounting device".

The attachment interface can also be referred to as a "mounting rail", "attachment rail" or "rail".

The term "rigidly connected" can also be referred to as "fixedly connected" or "permanently but detachably connected".

The coupling is configured to engage with the second portion 22 of the coupling attached to the operating table 20.

In an example, the second portion 22 of the coupling comprises a receiving space.

The receiving space can also be referred to as "accommodation".

In an example, the connection comprises at least two bearing points.

The patient support can also be referred to as an "assembly unit".

In an example, the holding device 10 is configured to: a) a shiftable holding on an assembly unit, such as a sliding movement; and b) a temporary fixation.

The accessory rail 12 is movably attached onto the assembly unit (or patient table) via the coupling. The second portion 22 of the coupling can also be provided as a fixed accessory rail, e.g. mounted to the patient table or patient support.

In an example, the sliding accessory rail 12 slides over the fixed (accessory) rail that is attached to the table.

In an example, the sliding accessory rail 12 is shiftable outside the fixed accessory rail at least partly to elongate the range of the equipment 18.

The rail(s) serve(s) as fixation point for modules.

In an example, the modules are attached shiftable to the accessory rails.

The operating table may also be referred to as "cathlab table".

In an example, the modules need to be relocated, for example simultaneously, because the modules, equipment and devices are (temporarily) needed at a different location.

In an example, most of the modules, equipment and devices require cables for power and/or earth and/or data and/or image data transmission to other locations or tubes for gas and/or liquid distribution to other locations.

In an example, the modules are arranged in a so-called work or operating position where the modules are "most frequently used" by a user, e.g. a physician.

In an example, the second portion 22 of the coupling is a European accessory rail. In another example, the second portion 22 of the coupling is a USA accessory rail. In a still further example, the second portion 22 of the coupling is an accessory rail according to a standardized norm.

In an example, the holding device further comprises a second portion 22 of the coupling forming the coupling together with the first portion 14 of the coupling, and the first portion 14 of the coupling is movable and the second portion 22 of the coupling is configured to be attached to the patient support 20. As an option, the attachment is a stationary attachment.

The term "stationary" can also be referred to as "fix".

The first portion 14 of the coupling can also be referred as "a connector". The second portion 22 of the coupling can also be referred to as a fixed accessory rail.

In an example, the first portion 14 of the coupling comprises a rail.

The rail of the first portion 14 of the coupling is connected to an interface of the second portion 22 of the coupling attached to the patient support 20.

In another example, the second portion of the coupling is a rail.

In an example, the rail is connected to an interface attached to the first portion 14 of the coupling attached to the holding device 10.

In an example, the accessory rail 12 is configured as a sliding accessory rail comprising a front side with an interface 16 configured as a rail profile; and a rear side with the receiving space. The receiving space is configured to receive a mounting device with said rail profile.

The receiving space can also be referred to as "accommodation", "notch", "channel" or "groove".

In an example, the connector comprises a at least partly constant cross-section.

In an example, a holding arrangement comprises a holding device according to one of the above examples and a mounting device. The holding device is attached movably to the mounting device. The mounting device is configured as a fixed accessory rail.

Figure 2:
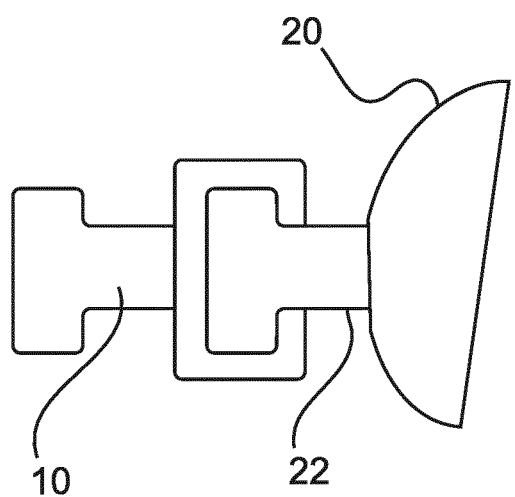
FIG. 2 shows a schematic vertical cross-section view of an example of a sliding accessory rail.

FIG. 2 shows the holding device serving as an adapter. The accessory rail is configured with a first cross-section or profile, e.g. a first standard cross-section or profile, in order to provide a first type of coupling interface for mounting of equipment, e.g. a first standard type of coupling interface; and the first portion of the coupling provides a second type of coupling interface, e.g. a first standard type of coupling interface, to be mounted to a second cross-section or profile, e.g. a second standard cross-section or profile. The holding device serves as an adapter between the first and the second type of coupling interface, e.g. between the first and the second standard type of coupling interface.

For example, a fixed rail can be provided with a first type of a standardized cross section. The first portion 14 of the coupling is provided to be mounted to that first type of a standardized cross section which acts as the second portion of the coupling. The accessory rail can then be provided with a second type of a standardized cross section. The holding arrangement thus serves as an adapter from one standard to another standard, for example from EU to US standard or vice versa.

The terms "EU or US standard" refer to standardized interfaces to allow attachment of a multitude of equipment. The standards may differ in size or proportion. The standards may also differ in the engagement of connecting concept.

The sliding accessory rail 12 may also be referred to as an adapter for mounting of the equipment 18 or modules.

In an example, the first portion of the coupling comprises an accommodation for a rail with a profile as the accessory rail, and the second portion 22 of the coupling comprises a rail with a profile of the accessory rail.

For example, in case an (existing) fixed accessory rail is already mounted at a patient table, a further accessory rail can be mounted. In such case, the fixed accessory rail acts as the second portions 22 of the coupling and the further accessory rail is mounted to the existing rail via the first portion 14 of the coupling.

The further accessory rail then provides the actual accessory rail for mounting of equipment.

If the fixed accessory rail is provided with a profile and dimensions according to one specific standard, such as for example (United States) US standard, and equipment according to a different standard, such as (European) EU standard shall be mounted, the further accessory rail can be provided according to this different standard. The further accessory rail thus provides a so-to-speak adapter function, for example from US- to EU-standard or vice versa.

The accessory rail can also serve as a prolongation of an existing (fixed) rail.

Figure 3:
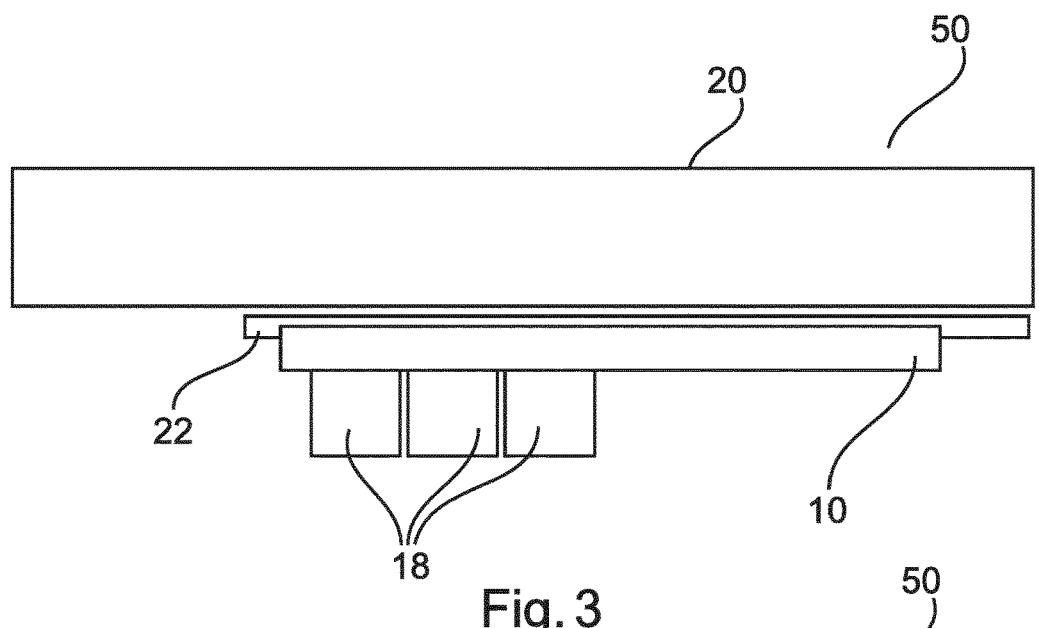
FIG. 3 shows a schematic perspective view of an example of a system for holding equipment at a patient support.

FIG. 3 shows a schematic perspective of a system 50 for holding equipment at a patient support. The system 50 comprises a holding device 10 according to one of the examples above. The system 50 also comprises a patient support 20. The holding device 10 is removably attached to the patient support 20, and equipment can be attached to the accessory rail. In relation to the patient support, the accessory rail is movable in a horizontal sliding movement.

In an option, equipment 18 is provided, e.g. as an equipment arrangement. The equipment 18 is attachable to the accessory rail, and can thereby be removably attached to the holding device 10. The holding device 10 is removably attached to the patient support 20. Furthermore, the equipment 18 comprises at least one of the group of monitor units, X-ray imaging units, ultrasound units, patient monitoring units and interventional tool operating units.

In an example, the patient support arrangement 20 comprises at least one of the group of a patient table, a patient stand and a patient seat.

The system 50 can also be referred to as a mounting device or mounting system.

The system/mounting system provides operational equipment at an operating table. The system comprises an operating table as an assembly unit, a holding device with at least one accessory rail and equipment.

In an example, the system provides at least one further accessory rail and/or at least one further holding device.

The accessory rails are equipped or charged with equipment, which are used for a certain aspect during an intervention and the interrelated modules attached to the holding device can be removed and substituted in one process step.

In an option, an arrangement of the equipment is provided on the accessory rail in a mounted configuration. In a first example, the arrangement of the equipment is movably in a horizontal sliding movement. In a second example, the arrangement of the equipment is detachable from the patient support while maintaining the mounted configuration on the accessory rail. In another example, the first and the second example are provided.

Figure 4A:
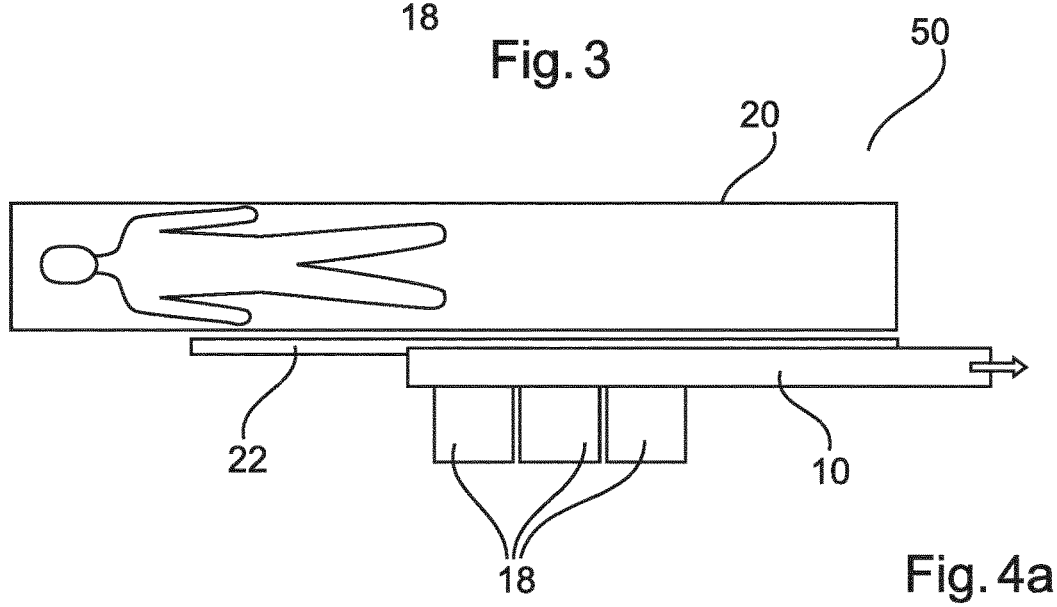
FIGS. 4a and 4b show a schematic perspective view of a shifting movement of a sliding accessory rail.
Figure 4B:
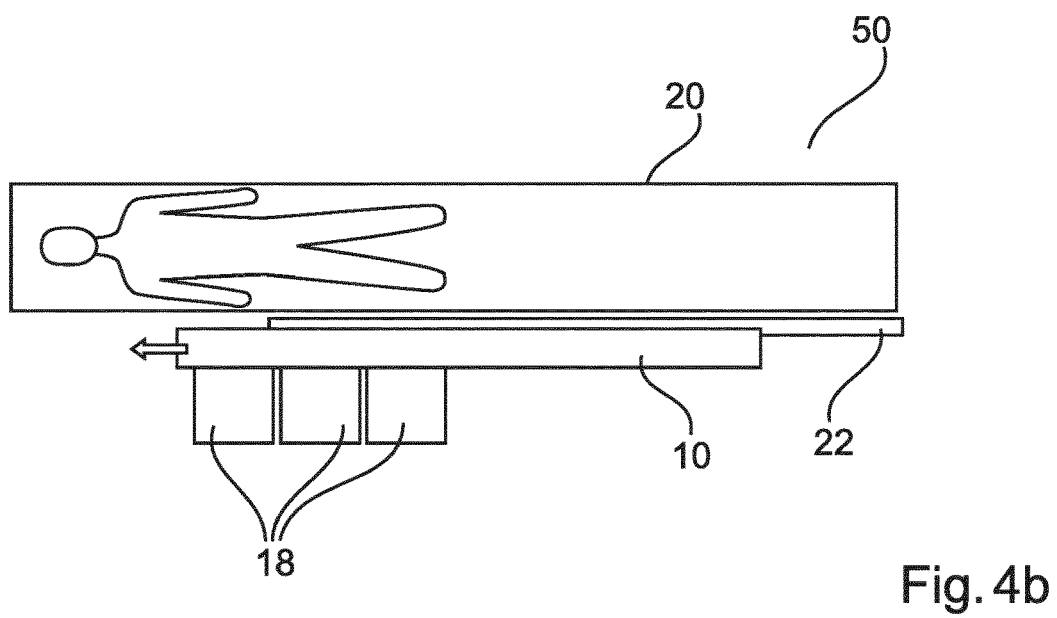

FIGS. 4a and 4b show a schematic perspective view of a shifting movement of a sliding accessory rail 12.

The provision of a movable connection allows, for example, to temporarily move or even remove the accessory rail 12 together with the mounted equipment 18. For example, during an intervention procedure, for certain phases, the equipment 18 is not needed, or a different configuration is needed, and wider access to the patient is required. The equipment 18 can then easily be removed and put back in place.

FIG. 4a shows a schematic perspective view with the equipment 18 shifted outside of the range for the physician. In FIG. 4b the same shifting movement in the opposite direction is shown.

In another example, indicated in FIGS. 4a and 4b, the second portion 22 of the coupling is a mounting rail attached to the patient support 20. The accessory rail of the holding device 10 is shiftable at least partly outside a range of the mounting rail to enlarge a range of mounted equipment. This is indicated in FIG. 4a with a little arrow pointing to the left.

In another example, not shown in detail, at least one further accessory rail is provided that is connected to a further first portion of the coupling. The further accessory rail is provided to be equipped with a further arrangement of the equipment provided on the accessory rail in a further mounted configuration.

Figure 5:
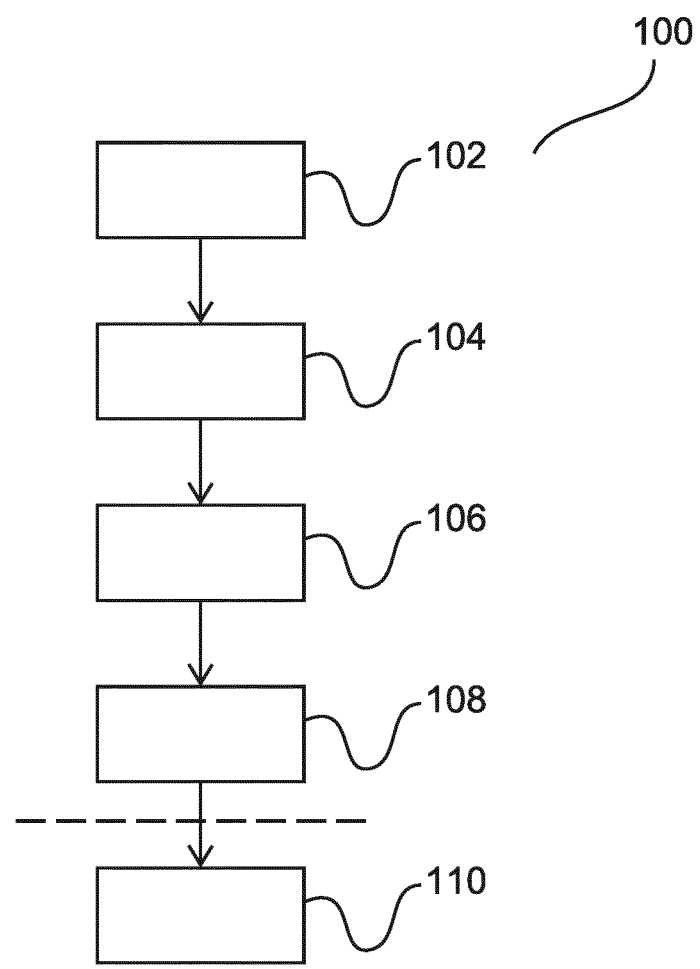
FIG. 5 shows an example of a method for removably providing equipment at a patient support.

FIG. 5 shows a method 100 for removably providing equipment at a patient support, comprising the following steps:

In a first step 102, also referred to as step a), an accessory rail that is rigidly connected to a first portion of a coupling of is provided; the accessory rail is configured as an attachment interface for temporal attachment of equipment at a patient support.

In a second step 104, also referred to as step b), the first portion is coupled to a second portion of the coupling attached to the patient support, such that, in interaction with the second portion of the coupling, a movable connection of the accessory rail to the patient support is provided.

As an option, in a third step 106, also referred to as step c1), equipment is temporally attached at a patient support by the attachment interface of the accessory rail.

As an option, provided alternative or in addition, the accessory rail is fixated for temporary fixing of the accessory rail in relation to the patient support.

In a fourth step 108, also referred to as step d), the accessory rail 12 is horizontally slided in relation to the patient support 20.

In a further option, as a fifth step 110, also referred to as step e), the accessory rail of the holding device is substituted with a further accessory rail.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:
1. A holding device, comprising:
an accessory rail; and
a first portion of a coupling;
wherein the accessory rail and a mounting rail are each configured as an attachment interface for temporary attachment of medical equipment at a patient support,
wherein the accessory rail is rigidly connected to the first portion of the coupling,
wherein the first portion of the coupling is configured to provide and maintain, in interaction with a second portion of the coupling, a movable connection that connects the accessory rail to the patient support,
wherein the second portion of the coupling comprises a front side with an interface configured to attach to the patient support and a rear side that is the mounting rail,
wherein the first portion of the coupling comprises a rear side that is the accessory rail and a front side configured with a receiving channel configured to receive the mounting rail of the second portion into the receiving channel and removably connect the accessory rail to the mounting rail,
wherein the movable connection is configured to provide a horizontal sliding movement of the accessory rail in relation to the patient support, wherein, while con- nected, the first portion of the coupling is configured to be movable in relation to the second portion of the coupling, wherein the movable connection is configured to position, via the horizontal sliding movement, the accessory rail to provide a prolongation of the connected mounting rail, and wherein the movable connection is configured to provide the horizontal sliding movement of the accessory rail with attached medical equipment while maintaining an energy or data connection to the attached medical equipment.

2. The holding device according to claim 1, wherein the attached medical equipment comprises at least one device from the group consisting of monitor units, X-ray imaging units, ultrasound units, patient monitoring units, and interventional tool operating units.

3. The holding device according to claim 1, wherein the first portion of the coupling is configured to provide, in interaction with the second portion of the coupling, a fixation for temporary fixing of the accessory rail in relation to the patient support.

4. The holding device according to claim 1,
wherein the accessory rail is shiftable at least partly outside a range of the mounting rail to enlarge a range of mounted medical equipment.

5. The holding device according to claim 1, wherein the receiving channel comprises an accommodation for a rail with a profile of the accessory rail, and the mounting rail has the profile of the accessory rail.

6. The holding device according to claim 1, wherein the accessory rail is configured with a first cross-section or profile in order to provide a first type of coupling interface for mounting of medical equipment; and the first portion of the coupling provides a second type of coupling interface to be mounted to a second cross-section or profile, and
wherein the holding device serves as an adapter between the first and the second type of coupling interface.

7. A system for holding medical equipment, the system comprising:
the holding device according to claim 1; and
the patient support,
wherein the holding device is removably attached to the patient support.

8. The system according to claim 7, further comprising medical equipment,
wherein the medical equipment is removably attached to the accessory rail of the holding device, and
wherein the medical equipment comprises at least one of the group of: monitor units, X-ray imaging units, ultrasound units, patient monitor and interventional tool operating units.

9. The system according to claim 7, wherein an arrangement of the medical equipment is provided on the accessory rail in a mounted configuration, and wherein the arrangement of the medical equipment is movable in a horizontal sliding movement and/or detachable from the patient support while maintaining the mounted configuration on the accessory rail.

10. The system according to claim 7, wherein at least one further accessory rail is provided that is connected to a further first portion of the coupling,
wherein the further accessory rail is adapted to be equipped with a second arrangement of the medical equipment provided on the accessory rail in a second mounted configuration.

11. The holding device according to claim 1, wherein the accessory rail provides an attachment length of at least a half of a patient table's length.

12. The holding device according to claim 1, wherein the second portion of the coupling is rigidly fixed to the patient support and corresponds to a first standard profile, and wherein the first portion of the coupling corresponds to a second standard profile that is different than the first standard profile.

13. A method for removably providing medical equipment at a patient support, comprising:
providing an accessory rail that is rigidly connected to a first portion of a coupling of a holding device, wherein the accessory rail and a mounting rail is are each configured as an attachment interface for temporary attachment of medical equipment at the patient support;
coupling the first portion of the coupling to a second portion of the coupling, such that, in interaction with the second portion of the coupling, a movable connection of the accessory rail to the patient support is provided and maintained,
wherein the second portion of the coupling comprises a front side with an interface configured to attach to the patient support and a rear side that is the mounting rail, and
wherein the first portion of the coupling comprises a rear side that is the accessory rail and a receiving channel configured to receive the mounting rail, and the coupling comprises receiving, by the receiving channel, the mounting rail into the receiving channel to removably connect the accessory rail to the mounting rail; and
horizontally sliding the accessory rail in relation to the patient support with attached medical equipment while maintaining an energy or data connection to the attached medical equipment and position the accessory rail to provide a prolongation of the connected mounting rail, wherein, while connected, the first portion of the coupling is movable in relation to the second portion of the coupling.

14. The method according to claim 13, further comprising:
temporarily attaching medical equipment at the patient support by the attachment interface of the accessory rail, and/or fixating of the accessory rail for temporary fixing of the accessory rail in relation to the patient support.

15. The method according to claim 13, further comprising substituting the accessory rail with a further accessory rail.

16. The method according to claim 13, wherein the accessory rail provides an attachment length of at least a half of a patient table's length.

17. The method according to claim 13, wherein the second portion of the coupling is rigidly fixed to the patient support and corresponds to a first standard profile, and wherein the first portion of the coupling corresponds to a second standard profile that is different than the first standard profile.

* * * * *